United States Patent [19]

Butler et al.

[11] Patent Number: 5,367,043

[45] Date of Patent: Nov. 22, 1994

[54] DURABLE FORMALDEHYDE-FREE PHENOLIC RESINS, AND METHOD OF PREPARING SUCH RESINS

[75] Inventors: John M. Butler, Dayton; Richard L. Brandon, Chillicothe, both of Ohio

[73] Assignee: Enzymol International, Inc., Columbus, Ohio

[21] Appl. No.: 788,791

[22] Filed: Nov. 6, 1991

[51] Int. Cl.$^5$ .................................. C08G 63/18
[52] U.S. Cl. .................................. 528/193; 528/205; 528/212; 528/218
[58] Field of Search .................. 528/193, 212, 218, 205

[56] References Cited

U.S. PATENT DOCUMENTS

| | | | |
|---|---|---|---|
| 4,226,800 | 10/1980 | Picklesimer | 260/465 |
| 4,463,147 | 7/1984 | Diethelm et al. | 526/262 |
| 4,525,572 | 6/1985 | Diethelm et al. | 528/170 |
| 4,647,952 | 3/1987 | Pokora et al. | 503/211 |
| 4,666,997 | 5/1987 | Renner et al. | 526/262 |
| 4,678,849 | 7/1987 | Liu et al. | 526/259 |
| 4,689,378 | 8/1987 | Chaudhari et al. | 526/259 |
| 4,745,166 | 5/1988 | Renner et al. | 526/259 |
| 4,749,767 | 6/1988 | Chaudhari et al. | 528/170 |
| 4,826,927 | 5/1989 | Schmid et al. | 525/422 |
| 4,885,403 | 12/1989 | Inbasekaran et al. | 568/651 |
| 4,900,671 | 2/1990 | Pokora et al. | 435/156 |
| 4,916,203 | 4/1990 | Pigneri et al. | 528/101 |
| 4,983,709 | 1/1991 | Jackson et al. | 528/230 |

OTHER PUBLICATIONS

Dirlkow, Stoil K. *High Performance Polym*, "Propargyl-terminated Resins" vol. (2)1, pp. 67–77, 1990.

*Primary Examiner*—John Kight, III
*Assistant Examiner*—Richard Jones
*Attorney, Agent, or Firm*—Thompson, Hine & Flory

[57] ABSTRACT

A curable formaldehyde-free phenolic resin having formula (I):

$$[(A)_a(B)_b]_n \qquad (I)$$

where A is

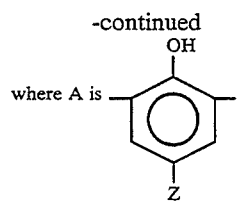

or

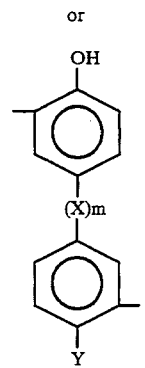

and B is

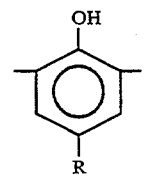

or (Abstract continued on next page.)

-continued

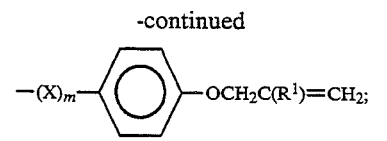

Y is —OCH$_2$C≡CH or —OCH$_2$C(R$^1$)=CH$_2$;

R$^1$ is hydrogen or methyl,

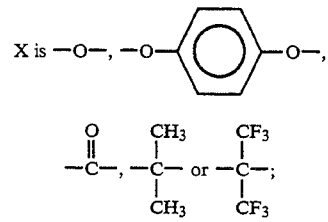

-continued

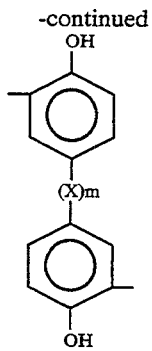

wherein a and b each represent an integer equal to or greater than 1, a+b multiplied by n is an integer of about 3 to 100;

m is 0 or 1; and R is hydrogen, halogen, alkyl having about 1 to 12 carbon atoms, aryl having about 6 to 12 carbon atoms, allyl having 3 or 4 carbon atoms, aralkyl having about 7 to 13 carbon atoms, alkaryl having about 7 to 13 carbon atoms, alkoxy having about 1 to 4 carbon atoms, aryloxy having about 6 to 12 carbon atoms, or Z is —OCH$_2$C≡CH, —OCH$_2$C(R$^1$)=CH$_2$,

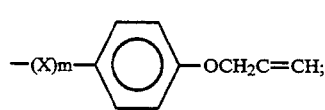

or

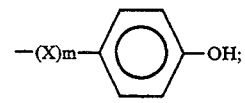

and methods for preparing such resin are described.

12 Claims, No Drawings

DURABLE FORMALDEHYDE-FREE PHENOLIC RESINS, AND METHOD OF PREPARING SUCH RESINS

BACKGROUND OF THE INVENTION

The present invention relates to novel phenolic resins and products derived therefrom which have improved thermal and oxidation stability. The resins do not give volatile products upon curing and do not involve the use of formaldehyde or formaldehyde-producing agents in their preparation.

Phenolic resins are well known and are generally prepared from phenols and formaldehyde. Such phenolic resins are cured by further reaction with formaldehyde or formaldehyde-producing compounds and/or by the residual methylol groups in the resin. The use of formaldehyde introduces environmental and toxicological problems in the preparation, fabrication, and even in the long term use of such materials. The reaction to form such resins introduces methylene bridges between the phenolic rings. These are points of attack for high temperature oxidative degradation. Most importantly the curing of conventional phenolic resins evolves water, alcohol and/or formaldehyde. This complicates the fabrication and these volatiles lead to voids in the cured resin. Such voids are highly detrimental to the mechanical properties of the resin, especially in high performance composite materials and adhesives such as those used in automotive, aircraft, and aerospace applications.

Recently, improved methods and processes for obtaining high molecular weight phenolic resins by enzymatic oxidation have been described in commonly assigned U.S. Pat. Nos. 4,647,952 and 4,900,671. These phenolic resins have the general formula

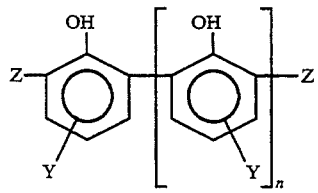

where Y is present in the meta or para position and is selected from the group consisting an alkyl group, a halogen atom (e.g., fluorine, chlorine or bromine), an aryl group, a phenylalkyl group, an alkoxy group, an allyl group, a group of the formula —COOR where R is hydrogen or a phenylalkyl group, an amino group of the formula —$NR_1R_2$ where $R_1$ and $R_2$ are the same or different and represent a hydrogen atom or an alkyl group; Z is a hydrogen atom, an alkyl group, a halogen atom, an aryl group, a phenylalkyl group, a —COOR group, or Z in conjunction with the adjacent meta position represents a condensed benzene ring which may be substituted or unsubstituted; and n is greater than or equal to 2.

Phenolic resins prepared by the oxidative coupling of phenols are generally superior to those phenolic resins prepared using formaldehyde. However, they do not have an inherent curing mechanism which is desirable in order for these resins to be useful for the preparation of composites, moldings, adhesives, coatings, and the like.

These resins have the phenolic units coupled directly to each other rather than through a methylene bridge as in conventional phenolic resins. Such systems overcome many of the disadvantages of conventional phenolic systems. However, to be useful for the preparation of composites, adhesives, moldings, or coatings they need to be "cured" or cross-linked, preferably without evolution of volatiles.

SUMMARY OF THE INVENTION

A principal object of the present invention is to provide a series of highly thermostable phenolic resins that cure without liberation of volatiles and do not require the use of formaldehyde or formaldehyde producing compounds in their preparations or cure.

Another object of the present invention is to provide a method by which these highly thermostable phenolic resins can be prepared.

Still another object of the present invention is to prepare composite materials, molding materials, adhesive compositions and coating compositions based on these highly thermostable phenolic resins.

In accordance with the present invention, these objects are achieved by incorporating either propargyl ether groups or allylic ether groups into phenolic resins, particularly phenolic resins prepared by enzymatic oxidation of phenols.

In one embodiment, the present invention relates to a curable formaldehyde-free phenolic resin having the formula (I):

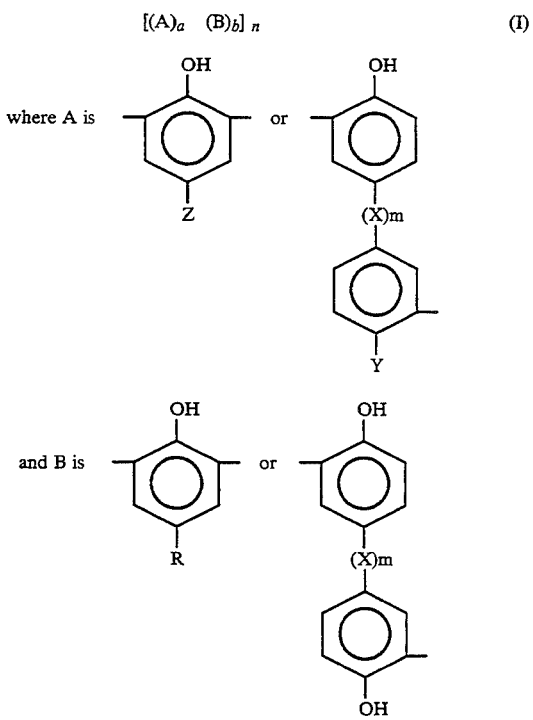

wherein a and b each represent an integer equal to or greater than 1, a+b multiplied by n is an integer of about 3 to 100;

Z is —$OCH_2C$=CH, —$OCH_2C(R^1)$=$CH_2$,

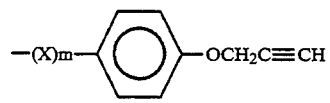

-continued
or

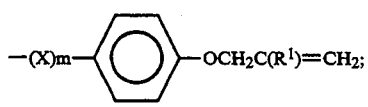

Y is —OCH$_2$C≡CH
or
—OCH$_2$C(R$^1$)=CH$_2$; R$^1$ is hydrogen or methyl;

X is —O—, 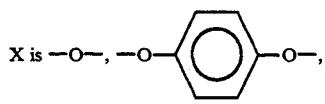,

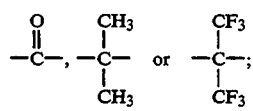;

m is 0 or 1; and R is hydrogen, halogen, alkyl having about 1 to 12 carbon atoms, aryl having about 6 to 12 carbon atoms, allyl having 3 or 4 carbon atoms, aralkyl having about 7 to 13 carbon atoms, alkaryl having about 7 to 13 carbon atoms, alkoxy having about 1 to 4 carbon atoms, aryloxy having about 6 to 12 carbon atoms, or

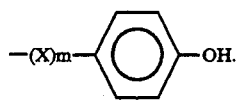

In accordance with a more preferred embodiment of the invention, the curable formaldehyde-free phenolic resin is represented by the formulas (II) through (XIII):

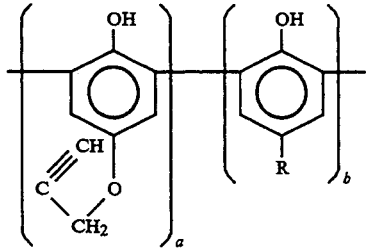 (II)

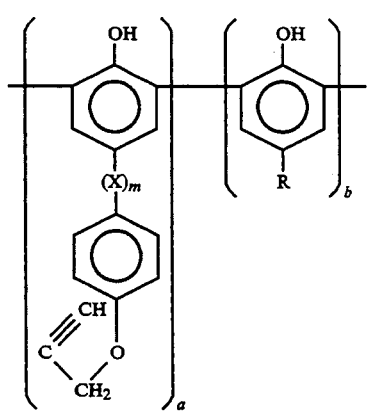 (III)

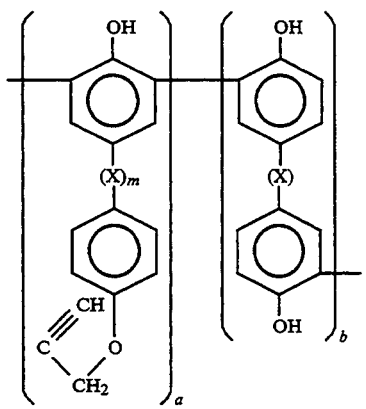 (IV)

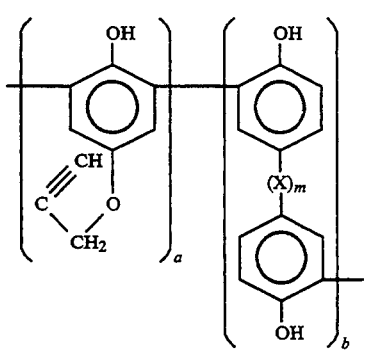 (V)

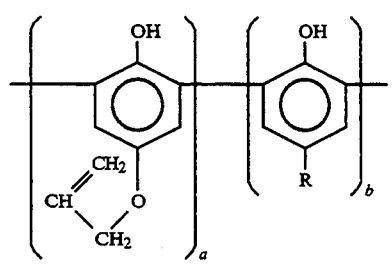 (VI)

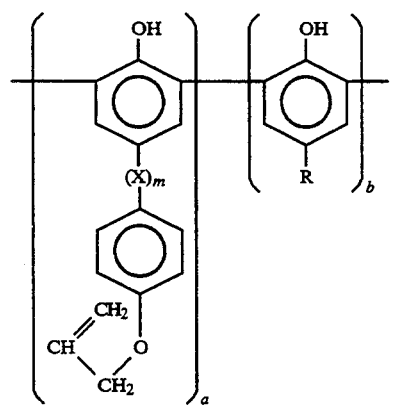 (VII)

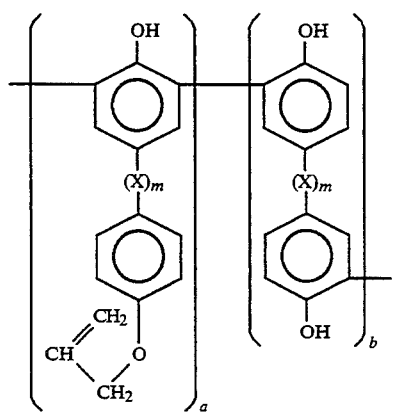
(VIII)

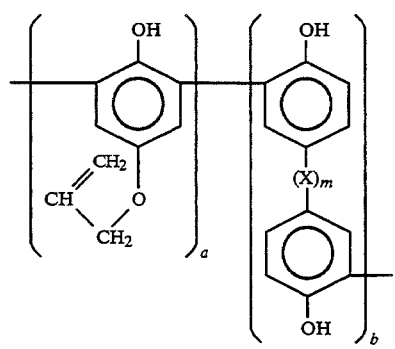
(IX)

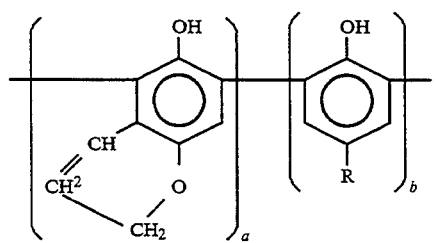
(X)

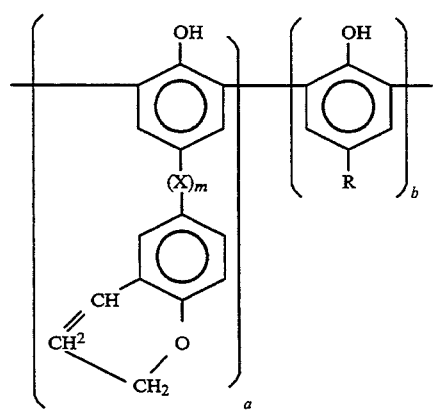
(XII)

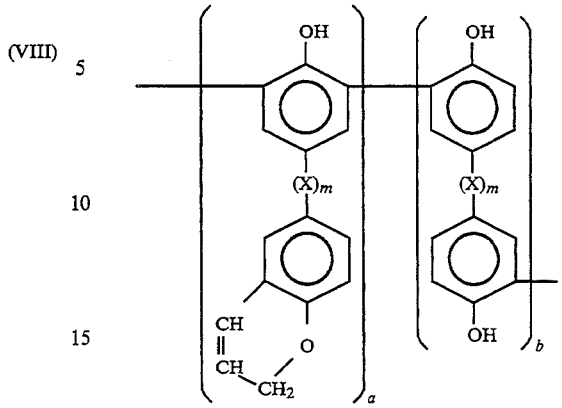
(XII)

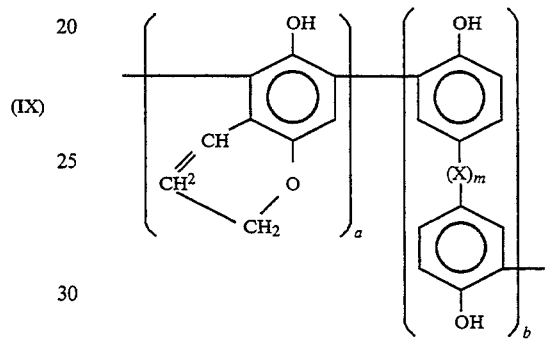
(XIII)

where a, b, X and m are defined as in claim 1.

Another embodiment of the present invention relates to a method for preparing a curable formaldehyde-free phenolic resin comprising oxidatively copolymerizing a first phenolic compound modified with a propargyl ether group or an allyl ether group having the formula (XIV) or (XV):

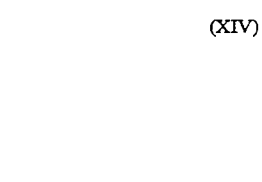
(XIV)

or

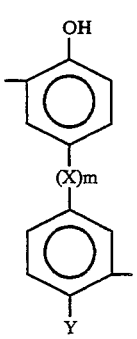
(XV)

with a second phenolic compound having the formula (XVI) or (XVII):

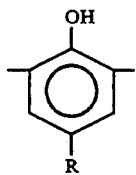

or

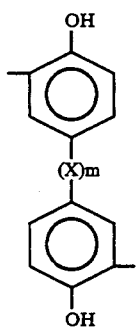

where Z is —OCH$_2$C≡CH, —OCH$_2$C(R$^1$)=CH$_2$,

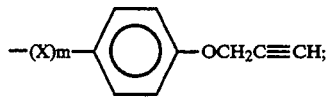

or

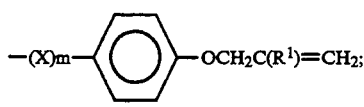

Y is —OCH$_2$C≡CH
or
—OCH$_2$CH(R$^1$)=CH$_2$; R$^1$ is hydrogen or methyl;

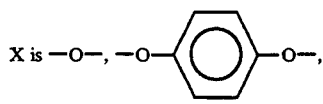

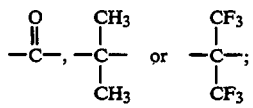

m is 0 or 1; and R is hydrogen, halogen, alkyl having about 1 to 12 carbon atoms, aryl having about 6 to 12 carbon atoms, allyl having 3 or 4 carbon atoms, aralkyl having about 7 to 13 carbon atoms, alkaryl having about 7 to 13 carbon atoms, alkoxy having about 1 to 4 carbon atoms, aryloxy having about 6 to 12 carbon atoms, or

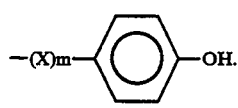

Preferably, the resin is copolymerized by the process described in U.S. Pat. No. 4,900,671, however, other oxidation coupling reactions can also be useful.

Yet another embodiment of the present invention relates to a method for preparing a curable formaldehyde-free phenolic resin which comprises reacting a formaldehyde-free polyphenol resin with a propargyl halide or an allyl halide to incorporate the respective propargyloxy groups or allyloxy groups on at least a portion of the pendant polyphenols.

DETAILED DESCRIPTION OF THE INVENTION

The curable formaldehyde-free phenolic resins of the present invention are prepared by incorporating into the resin certain reactive groups such as propargyl or allyl ether groups. The propargyl or allyl ether groups are capable of undergoing addition reactions without evolution of volatiles to yield thermal and oxidation stable crosslinks. The propargyl or allyl ether groups can be incorporated into the phenols before polymerization or they can be introduced into the polymer after polymerization.

Aromatic propargyl ethers and methods for preparing such ethers are well known. Specific references which describe the preparation of aromatic propargyl ethers include U.S. Pat. Nos. 4,226,800; 4,885,403; 4,916,203; and 4,983,709.

It is generally desirable to control the degree of crosslinking of the phenolic resin to obtain optimum properties. This can be accomplished by copolymerizing phenols which have been modified to contain propargyl or allylic functions with nonreactive phenols such as:

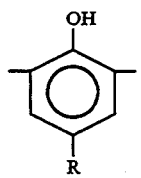

wherein R is defined as above.

These copolymers can be random copolymers or block copolymers wherein the modified phenols and the unmodified phenols appear in the structure randomly or in segments.

Aromatic propargyl and allyl ethers are readily prepared by reaction of the phenol in an organic solvent such as acetone, tetrahydrofuran, and the like, with propargyl or allyl halide. The halide is preferably a bromide or chloride. The raw materials are commercially available and the yields are near quantitative.

The preferable aromatic ethers are mono-ethers of bi-phenols prepared by using an excess of the bi-phenol and/or by adding the propargyl allyl halide to the bi-phenol solution so that there is always an excess of the bi-phenol. The mono-ether can be separated from the unreacted bi-phenol and any di-ether by their differences in solubility. In practice it is often unnecessary to separate the products.

Instead of preparing the propargyl or allyl substituted phenols and polymerizing them, one can preferably carry out the polymerization of a phenol or a phenol mixture and introduce the propargyl or allyl ether groups into the polymer so that the propargyl or allyl ether groups are incorporated onto at least a portion of the polyphenols. Thus, a solution of a polyphenol can be reacted with a propargyl halide or an allyl halide to produce a solution of a curable phenolic polymer. It is not necessary to isolate the polymer from the polymerization solution prior to reaction to introduce the propargyl or allyl groups. The resulting propargyl or allyl modified resins can be cured thermally with or without free radical initiators or catalysts.

These curable resins having a molecular weight of about 500 to 15,000 can then be used in a conventional manner to prepare composites, moldings, adhesives, and coatings.

Aryl propargyl ether containing resins condense without liberation of volatiles to yield very thermally and oxidatively stable products. The unusual stability of the products is believed to be due to a two-stage reaction where, at temperatures of 170°–180° C., the first stage reaction occurs to give the chromene structure with a significant shrinkage of the resin. At 200° C. the crosslinking addition reaction takes place with a minimum of shrinkage. Final postcuring at temperatures of about 250° C. are generally employed to give optimum high temperature stability. The propargyl ether first cyclizes to a chromene structure and this product then further condenses by additional polymerization with no by-products.

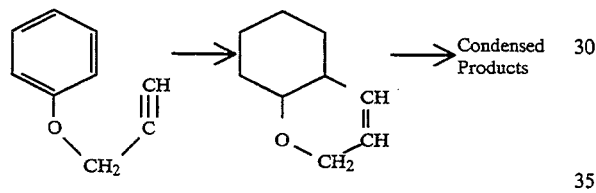

Such structures are more stable than structures that contain non-cyclic aliphatic linkages.

The modified resins and particularly the allyl modified resins can be co-cured with other monomers such as maleic or fumaric derivatives, e.g., maleimides. An especially desirable allyl modified phenolic resin is a composition from an allyl substituted polyphenol which is co-cured with an aromatic bismaleimide such as 1,1'-(methylene-di-4,1-phenylene) bismaleimide.

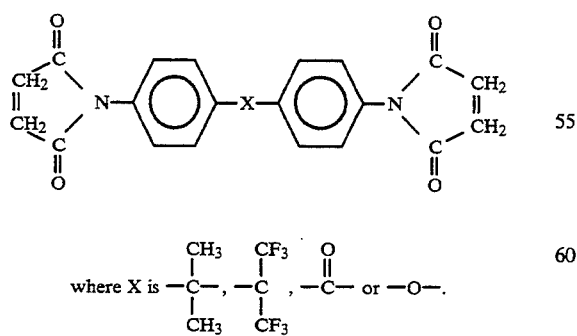

Typical allyl-, propargyl- and chromene-containing phenolic units that can be incorporated into the enzymatic oxidatively polymerized phenolic resins include

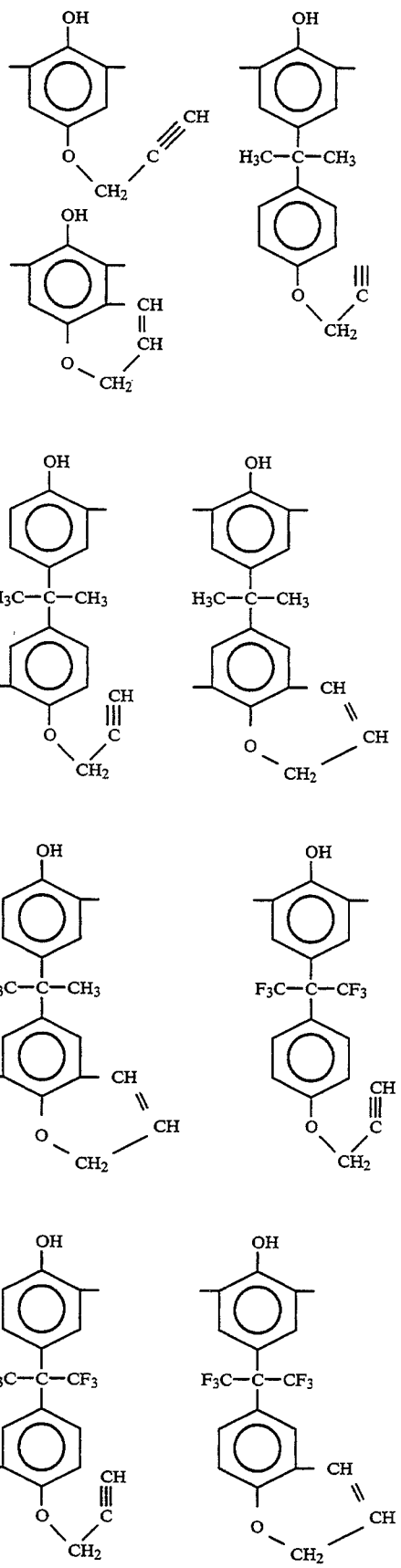

-continued
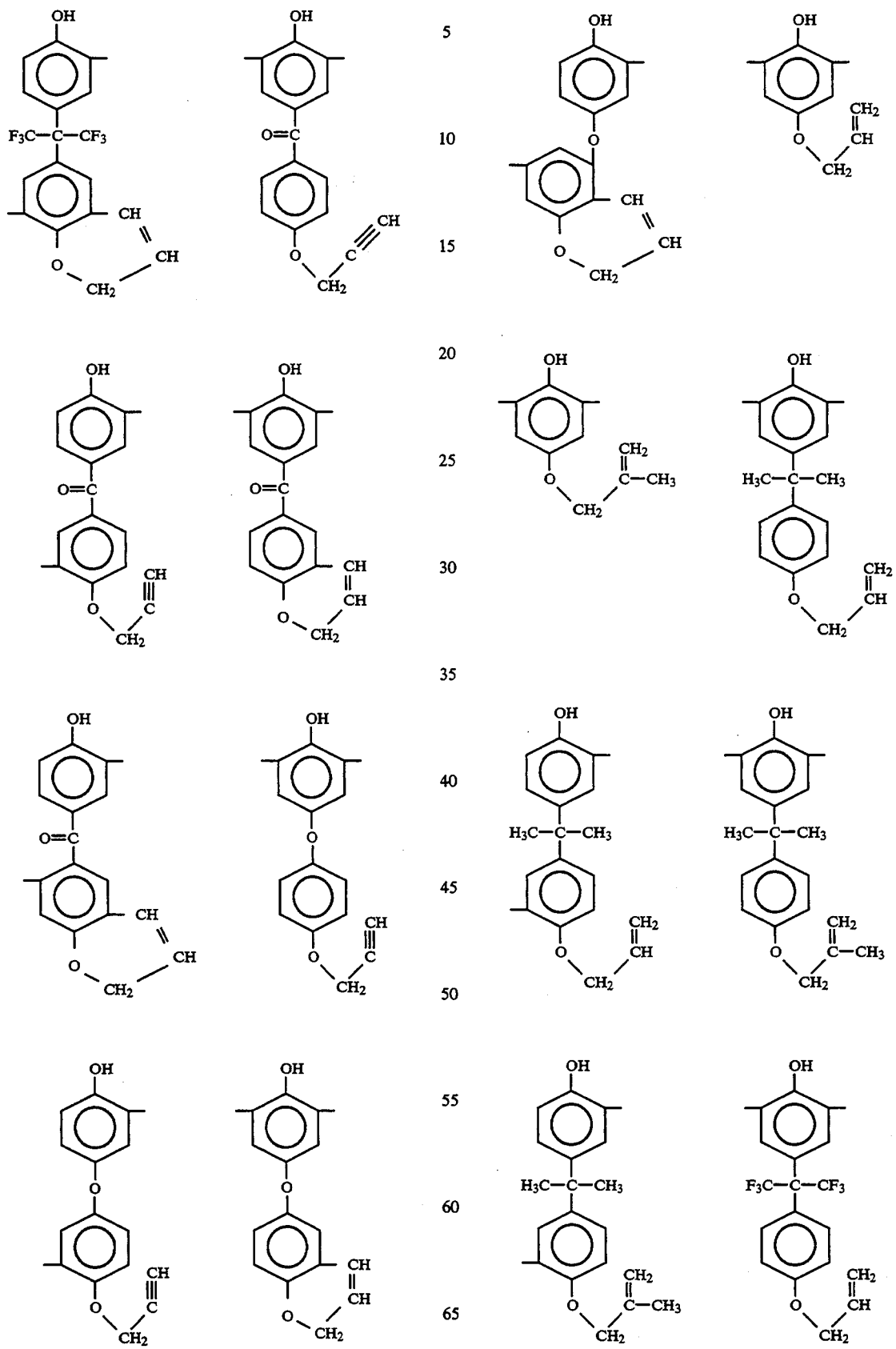

-continued

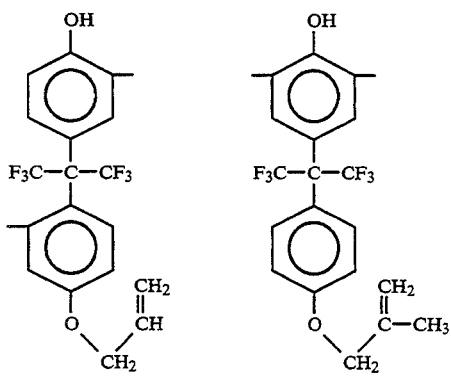
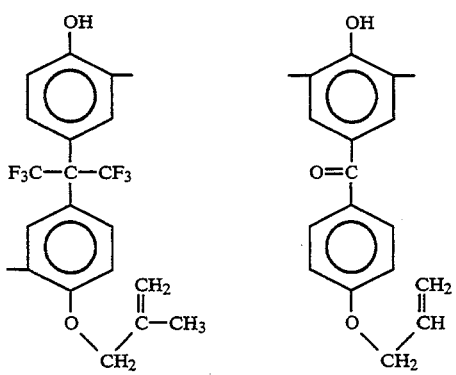
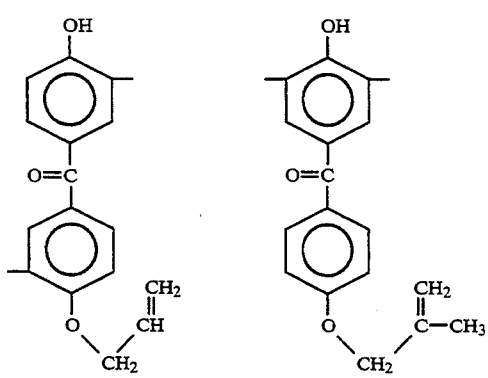
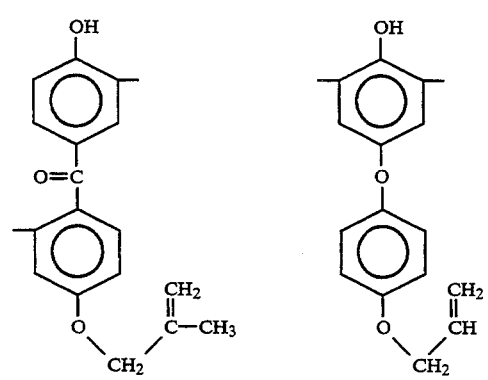

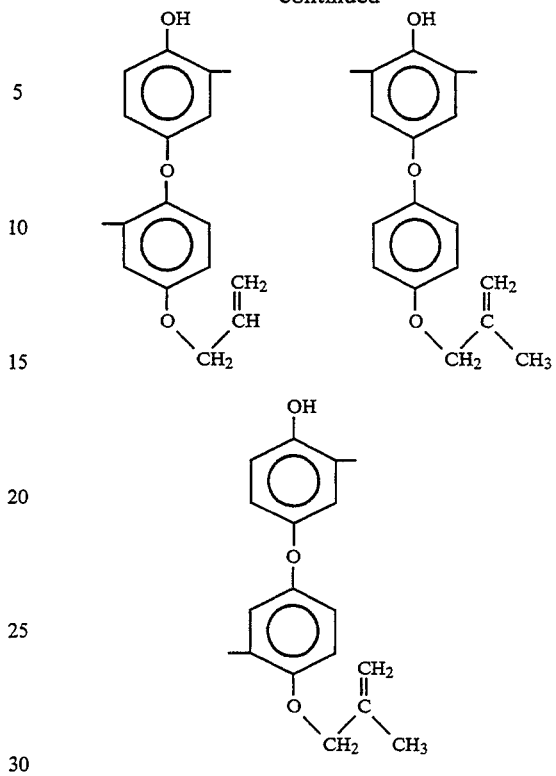

The invention is illustrated in more detail by the following non-limited example.

EXAMPLE

A solution of bisphenol A in acetone is reacted with less than one-half the equivalent of propargyl bromide and a corresponding amount of $K_2CO_3$ to give a mixture containing substantially the mono-ether of bisphenol A with small amounts of the bis-ether and some unreacted bisphenol A. This solution is then subjected to enzymatic oxidation polymerization by procedures well known to those skilled in the art. Thus, the pH is adjusted and buffered, the solvent concentration is adjusted, and an aqueous solution of peroxidase is added with controlled stirring, aqueous hydrogen peroxide is added at a controlled rate to ensure that a large excess of peroxide does not occur.

At the completion of the reaction, the organic phase containing the reactive, curable polyphenol resin is separated. This is accomplished by precipitation into a large volume of water. Alternatively, the organic solvent can be stripped by heat and/or vacuum. The organic solution can be used directly for preparing prepregs of fibrous materials for composites or for adhesive or coating applications.

Following evaporation of the solvent, the temperature is raised to about 170°–180° C. for several hours to convert the propargyl ether groups to the chromene structure. This reaction does not cause crosslinking so the materials are still soluble and fusible and thus can be used for fabrication.

After preparation of the propargyl ether, as described above, and before oxidation polymerization, additional bisphenol A can be added to the solution to permit formation of copolymers.

Having described the invention in detail and by reference to preferred embodiments thereof, it will be apparent that modifications and variations are possible without departing from the scope of the invention defined in the appended claims.

What is claimed is:

1. A curable formaldehyde-free phenolic resin having the formula (I):

$$[(A)_a (B)_b]_n \quad (I)$$

where A is 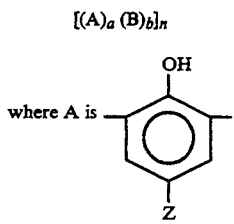

or

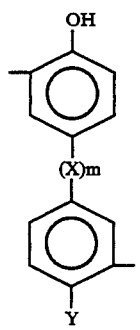

and B is

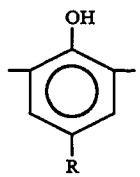

or

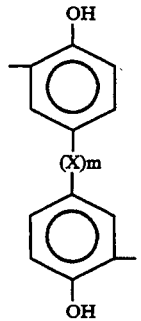

wherein a and b each represent an integer equal to or greater than 1, a+b multiplied by n is an integer of about 3 to 100;

Z is —OCH$_2$C≡CH, —OCH$_2$C(R$^1$)=CH$_2$,

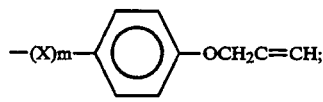

or

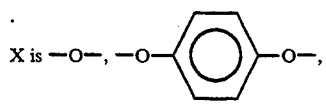

Y is —OCH$_2$C≡CH or —OCH$_2$C(R$^1$)=CH$_2$;

R$^1$ is hydrogen or methyl,

X is —O—, 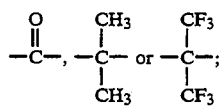,

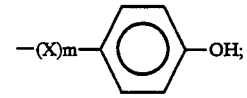;

m is 0 or 1; and R is hydrogen, halogen, alkyl having about 1 to 12 carbon atoms, aryl having about 6 to 12 carbon atoms, allyl having 3 or 4 carbon atoms, aralkyl having about 7 to 13 carbon atoms, alkaryl having about 7 to 13 carbon atoms, alkoxy having about 1 to 4 carbon atoms, aryloxy having about 6 to 12 carbon atoms, or

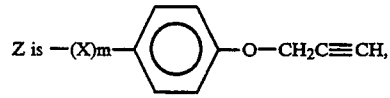

2. The resin of claim 1 wherein

Z or Y is —OCH$_2$C≡CH or

Z is 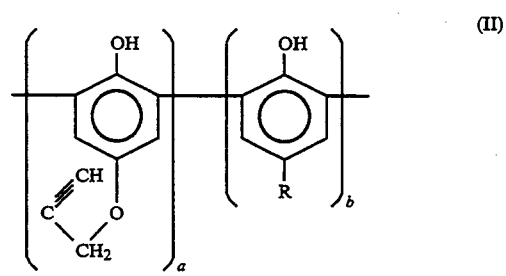, said resin being heated to a temperature of about 170° to 180° C. to cyclize the —OCH$_2$C=CH groups so as to form an oxygen-containing six member ring fused to the aromatic ring.

3. The resin of claim 1 having a formula (II)–(V):

(II)

where a, b and R are defined as in claim 1;

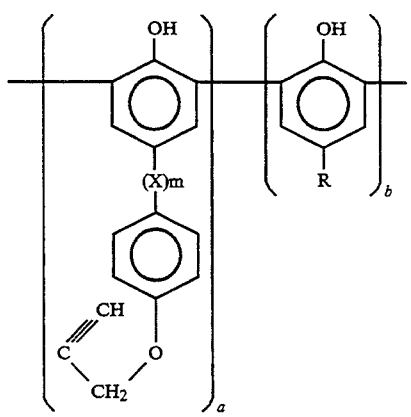
(III)
where a, b, R, X and m are defined as in claim 1;
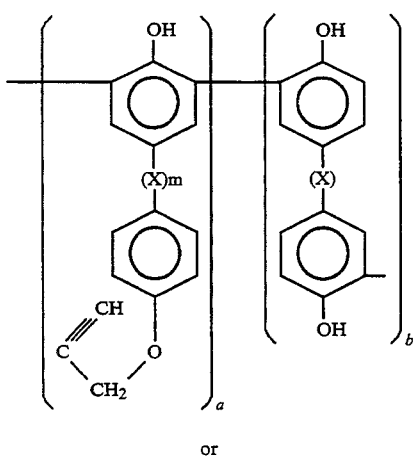
(IV)
or
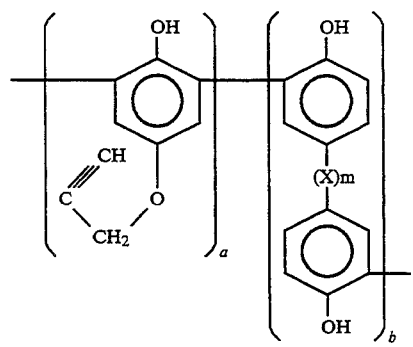
(V)
where a, b, X and m are defined as in claim 1.
4. The resin of claim 1 having a formula (VI)–(IX):
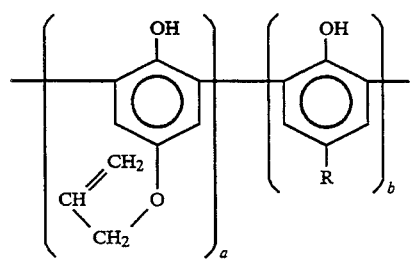
(VI)
where a, b and R are defined as in claim 1;
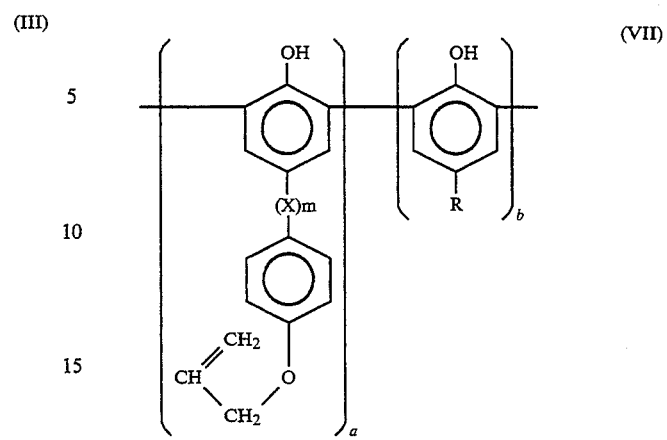
(VII)
where a, b, R, X and m are defined as in claim 1;
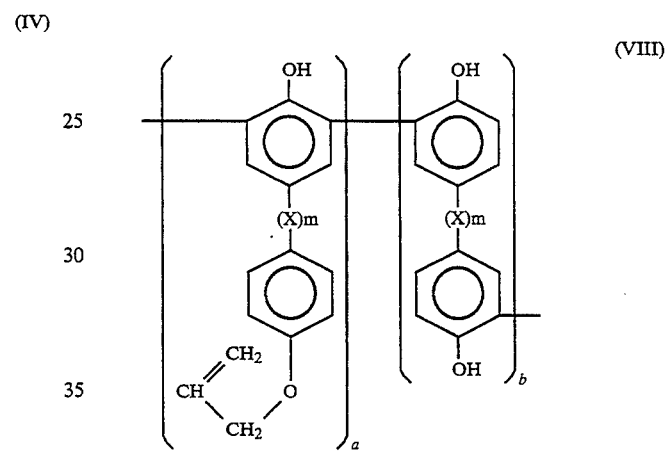
(VIII)
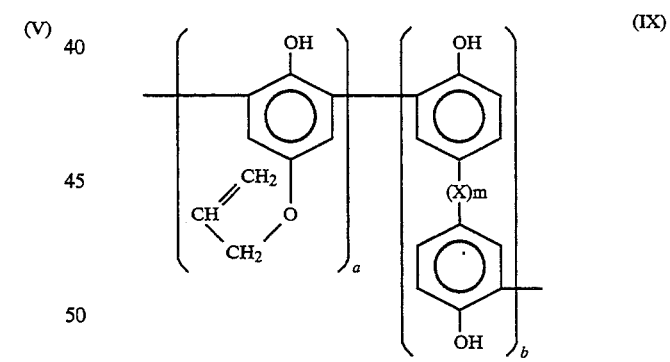
(IX)
where a, b, X and m are defined as in claim 1.
5. The resin of claim 2 having a formula (X)–(XII):
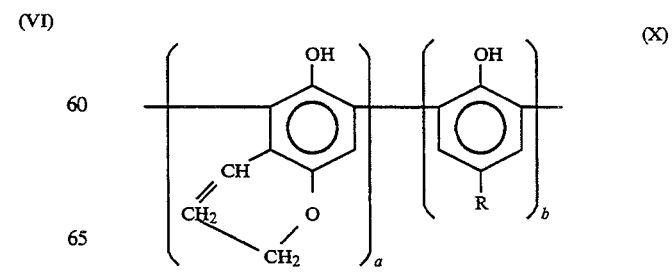
(X)
where a, b and R are defined as in claim 1;

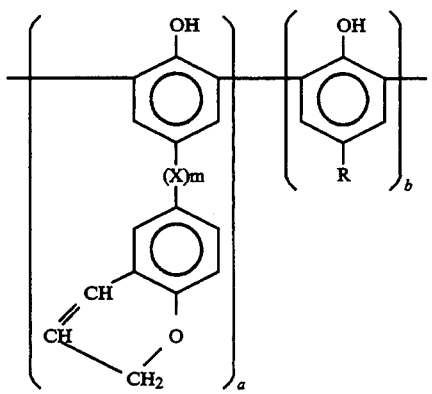
(XI)

where a, b, R, X and m are defined as in claim 1;

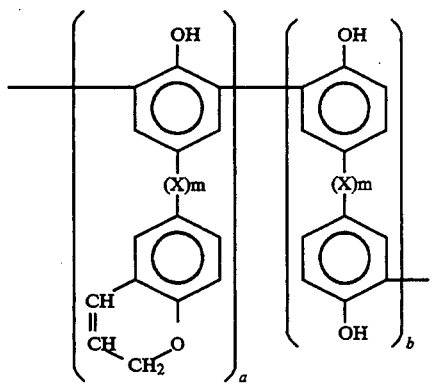
(XIIp)

where a, b, X and m are defined as in claim 1; or

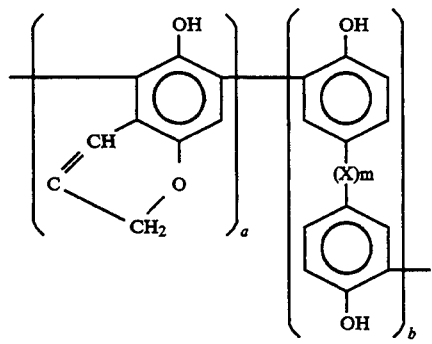
(XIII)

where a, b, X and m are defined as in claim 1.

6. A method for preparing a curable formaldehyde-free phenolic resin having the formula

[(A)$_a$(B)$_b$]$_n$      (I)

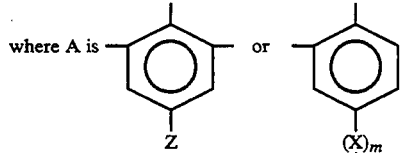

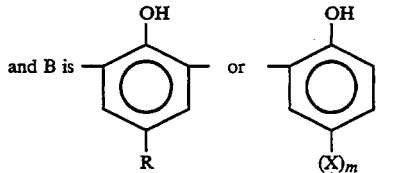

wherein a and b each represent an integer equal to or greater than 1, a+b multiplied by n is an integer of about 3 to 100;

Z is —OCH$_2$C≡CH, —OCH$_2$C(R$^1$)=CH$_2$,

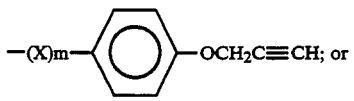

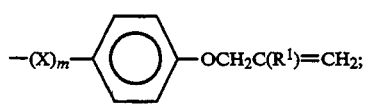

Y is —OCH$_2$C≡CH or —OCH$_2$C(R$^1$)=CH$_2$;

R$^1$ is hydrogen or methyl,

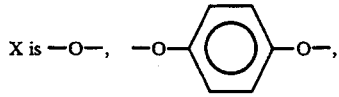

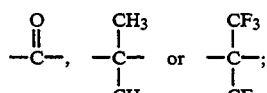

m is 0 or 1; and R is hydrogen, halogen, alkyl having about 1 to 12 carbon atoms, aryl having about 6 to 12 carbon atoms, allyl having 3 or 4 carbon atoms, aralkyl having about 7 to 13 carbon atoms, alkaryl having about 7 to 13 carbon atoms, alkoxy having about 1 to 4 carbon atoms, aryloxy having about 6 to 12 carbon atoms, or

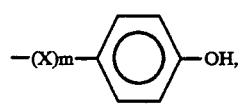

said method comprising:

reacting a first phenol having the structure (B) as defined in formula (I) or a mixture thereof with a propargyl halide to form one or more propargyloxyphenols, or reacting said phenol or mixture thereof with an allyl halide to form one or more allyloxyphenols;

copolymerizing said one or more propargyloxyphenols or said one or more allyloxyphenols with a second phenol having the structure (B) as defined in formula (I), said first phenol and said second phenol being the same or different, to provide said curable formaldehyde-free phenolic resin; and recovering said curable formaldehyde-free phenolic resin.

7. The method of claim 6 which comprises reacting said first phenol with less than the stoichiometric amount of said propargyl halide or said allyl halide to form a mixture containing a pre-determined ratio of said first phenol to said propargyloxyphenol or said allyloxyphenol;

copolymerizing said mixture of phenol and propargaryloxyphenol or allyloxyphenol to provide a curable formaldehyde-free phenolic resin containing a pre-determined ratio of phenolic groups to propargyloxyphenolic groups or allyloxyphenolic group; and recovering the curable formaldehyde-free phenolic resin.

8. The method of claim 6 wherein said curable formaldehyde-free phenolic resin is prepared by enzymatic oxidative coupling of said propargyl oxyphenol or said allyl oxyphenol with said phenol.

9. The method of claim 6 wherein said curable formaldehyde-free phenolic resin is capable of being cured catalytically or thermally at a temperature of about 200° to 250° C. to provide a cured resin which exhibits high oxidation and thermal stability.

10. The method of claim 6 wherein said curable formaldehyde-free phenolic resin is prepared by the reaction of said first phenol and said allyl halide, said resin capable of being co-cured in the presence of a maleimide.

11. The method of claim 6 wherein said curable formaldehyde-free phenolic resin is prepared by the reaction of said first phenol and said propargyl halide.

12. The method of claim 11 wherein said curable formaldehyde-free phenolic resin is heated to a temperature of about 170° to 180° C. to cyclize the —O CH$_2$C≡CH groups to form an oxygen-containing six member ring fused to the aromatic ring.

* * * * *